United States Patent [19]
Ringlien

[11] Patent Number: 6,067,155
[45] Date of Patent: May 23, 2000

[54] OPTICAL INSPECTION OF TRANSPARENT CONTAINERS USING INFRARED AND POLARIZED VISIBLE LIGHT

[75] Inventor: James A. Ringlien, Maumee, Ohio

[73] Assignee: Owens-Brockway Glass Container Inc., Toledo, Ohio

[21] Appl. No.: 08/997,987

[22] Filed: Dec. 24, 1997

[51] Int. Cl.[7] .............. G01N 21/00; G01N 9/04; G01J 4/00; H01L 27/00

[52] U.S. Cl. .............. 356/240; 356/73; 356/239; 356/365; 250/223; 250/208.1; 250/225

[58] Field of Search .............. 356/240, 427, 356/237, 364, 73, 239, 365; 250/223, 208.1, 225

[56] References Cited

U.S. PATENT DOCUMENTS

| | | |
|---|---|---|
| 1,681,991 | 8/1928 | Littleton, Jr. . |
| 1,934,187 | 11/1933 | Glasgow et al. . |
| 3,963,348 | 6/1976 | Nakatani et al. .............. 356/33 |
| 4,026,656 | 5/1977 | Kusz et al. .............. 356/51 |
| 4,283,145 | 8/1981 | Miyazawa .............. 356/240 |
| 4,547,067 | 10/1985 | Watannabe .............. 356/239 |
| 4,902,137 | 2/1990 | Krieg et al. .............. 356/427 |
| 4,908,507 | 3/1990 | Imre et al. .............. 356/240 |
| 5,095,204 | 3/1992 | Novini .............. 356/240 |
| 5,141,110 | 8/1992 | Trischan et al. .............. 356/240 |
| 5,444,237 | 8/1995 | Takizawa .............. 356/240 |
| 5,444,535 | 8/1995 | Axelrod . |
| 5,466,927 | 11/1995 | Kohler et al. .............. 356/240 |
| 5,502,559 | 3/1996 | Powell et al. .............. 356/73 |
| 5,536,935 | 7/1996 | Klotzsch et al. .............. 356/240 |

FOREIGN PATENT DOCUMENTS

| | | |
|---|---|---|
| 2323143 | 8/1976 | France . |
| 2437616 | 9/1979 | France . |
| 3705143 | 2/1987 | Germany . |
| 3840005 | 11/1988 | Germany . |
| 9746329 | 12/1997 | WIPO . |

Primary Examiner—Robert H. Kim
Assistant Examiner—Roy M. Punnoose

[57] ABSTRACT

Infrared and visible light energies are directed through a container onto a CCD camera that is responsive to both the visible and infrared light energy. Crossed polarizers are positioned on opposed sides of the container, and operate on the visible light energy in such a way as to block transmission of visible light to the camera in the absence of stress variations in the container, which alter polarization of the visible light energy traveling through the container. On the other hand, the polarizers have little or no effect on the infrared light energy, which creates a normally gray intensity of background light at the camera. In this way, incidence of visible light on the camera due to stress variations in the container appears as a bright signal against a normally gray background, while blockage of infrared light due to opaque variations in the container appears as a dark signal against the normally gray background.

23 Claims, 2 Drawing Sheets

OPTICAL INSPECTION OF TRANSPARENT CONTAINERS USING INFRARED AND POLARIZED VISIBLE LIGHT

The present invention is directed to inspection of transparent containers for commercial variations that affect the optical properties of the containers, and more particularly to a method and apparatus for inspecting the containers for stress and non-stress variations in the container sidewall and bottom.

BACKGROUND AND OBJECTS OF THE INVENTION

In the manufacture of transparent containers such as glass bottles and jugs, various types of anomalies can occur in the sidewalls, heels, bottoms, shoulders and/or necks of the containers. These anomalies, termed "commercial variations" in the art, can affect commercial acceptability of the containers. It has heretofore been proposed to employ electro-optical inspection techniques for detecting commercial variations that affect the optical properties of the containers. The basic principle is that a light source is positioned to direct light energy onto the container, and a camera is positioned to receive an image of the portion of the container illuminated by the light source. The light source may be of uniform intensity, or may be configured to have an intensity that varies across one dimension of the light source. Opaque and refractive commercial variations in the portion of the container illuminated by the light source are detected as a function of light intensity in the image of the illuminated container received and stored at the camera.

A problem is encountered in the manufacture of glass containers from recycled glass in that materials having different thermal expansion characteristics can become mixed in a single container. For example, it has been found that clear cookware, having very low thermal expansion characteristics, can become mixed with the glass for recycling. Any unmelted particles of the cookware that appear in the container create stress points on cooling that can fracture or become sites for later failures. Other inhomogeneities that can appear in the glass and cause stress variations include stones or bits of refractory material from the glass forehearth or spout. It is thus necessary to provide a method and system for detecting stress and opaque non-stress variations in the containers.

It has heretofore been proposed to employ crossed polarizers for detecting stress variations in the sidewalls of containers. Light energy directed through the crossed polarizers, and through a container positioned between the crossed polarizers, normally presents a dark field at the imaging camera in the absence of stress variations in the container sidewalls. However, a stress variation alters polarization of the light energy passing through the container sufficiently to present a bright spot at the camera against the otherwise dark background, indicative of the stress variation. See U.S. Pat. No. 4,026,656, assigned to the assignee hereof, which discusses such technology by way of background, and which proposes to employ infrared light energy and infrared polarization filters to reduce the background effects of ambient light.

It is a general object of the present invention to provide a method and apparatus for inspecting transparent glass articles, particularly glass containers, for commercial variations that affect optical characteristics of the containers. A more specific object of the present invention is to provide a method and apparatus of the described character that are particularly well suited for detecting both stress variations and opaque variations (stress and non-stress) in the container. Another object of the present invention is to provide a method and apparatus of the described character for detection of stress and opaque non-stress variations in containers at a single inspection station, with a single light source and a single light sensor. A further object of the present invention is to provide a method and apparatus of the described character that are economical to implement and reliable over an extended operating lifetime.

SUMMARY OF THE INVENTION

The present invention proposes to direct both infrared and visible light energy through a container onto a camera that is responsive to both visible and infrared light energy. Crossed polarizers are positioned on opposed sides of the container, and operate on the visible light energy in such a way as to block transmission of visible light to the camera in the absence of stress variations in the container, which alter polarization of the visible light energy traveling through the container. On the other hand, the polarizers have little or no effect on the infrared light energy, which creates a normally gray intensity of background light at the camera. In this way, incidence of visible light on the camera due to stress variations in the container appears as bright signals against a normally gray background, while blockage of infrared light due to opaque variations in the container appears as dark signals against the normally gray background.

In accordance with one aspect of the present invention, there is therefore provided a method of inspecting a container for commercial variations that affect optical characteristics of the containers, in which light energy is directed onto the container in such a way that a first wavelength of light energy (e.g., polarized visible light energy) is responsive to a first type of commercial variation in the container (e.g., stress variations), and a second wavelength of the light energy different from the first wavelength (e.g., infrared light energy) is responsive to a second type of commercial variation different from the first type (e.g., opaque variations). The light energy from the container is directed onto light sensing means, and commercial variations are detected as a function of light energy at the first and second wavelengths incident on the light sensing means. The light sensing means preferably takes the form of a single light sensor responsive to light energy at both of the first and second wavelengths, which preferably are directed onto the container and thence onto the sensor simultaneously. Light energy received at the sensor at the first wavelength is compared to light energy received at the second wavelength, preferably by forming an image of light energy at the sensor at the first wavelength against a background of energy at the sensor at the second wavelength. The light sensor in the preferred embodiments of the invention comprises a CCD array sensor that is scanned at increments of container rotation to provide a two-dimensional image of the inspected portion of the container that consists of light energy received at the first wavelength against a background of light energy received at the second wavelength.

In the preferred embodiments of the invention, the light energy at the first wavelength comprises polarized visible light energy responsive to stress variations in the container, while light energy at the second wavelength comprises infrared light energy responsive to opaque variations at the container. The terms "visible" and "infrared" light energies are used in their conventional senses. Visible light energy is light energy within the wavelength range of about 0.4 to 0.7 or 0.8 micrometers. Infrared light energy, which includes near-infrared light energy in accordance with the present invention, has a wavelength within the range of about 0.7 to 300 micrometers. Glass, however, becomes opaque at about 5 micrometers, which establishes an effective upper limit in such applications. The presently preferred silicon camera is sensitive up to about 1.1 micrometers. Light energy in both wavelength ranges is generated in the preferred embodiments of the invention by a broad area diffuse light source, and is incident on a CCD area array sensor that is responsive to both visible and infrared light energy.

Apparatus for detection of stress variations and opaque variations in glass articles such as containers in accordance with another aspect of the present invention comprises a light sensor for producing electrical signals responsive to light energy incident thereon in both the visible and infrared ranges. Infrared light energy is directed through a container onto the light sensor in such a way as to create at the light sensor a normally gray background, and such that opaque variations in the container appear as dark signals against the gray background. Visible light energy is directed through crossed polarizers disposed on opposite sides of the container and onto the light sensor in such a way that stress variations in the container appear as bright signals against the gray background at the sensor. The stress and opaque variations are thus detected as a function of the bright and dark signals against the gray background at the sensor.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF THE PREFERRED EMBODIMENTS

Figure 1:
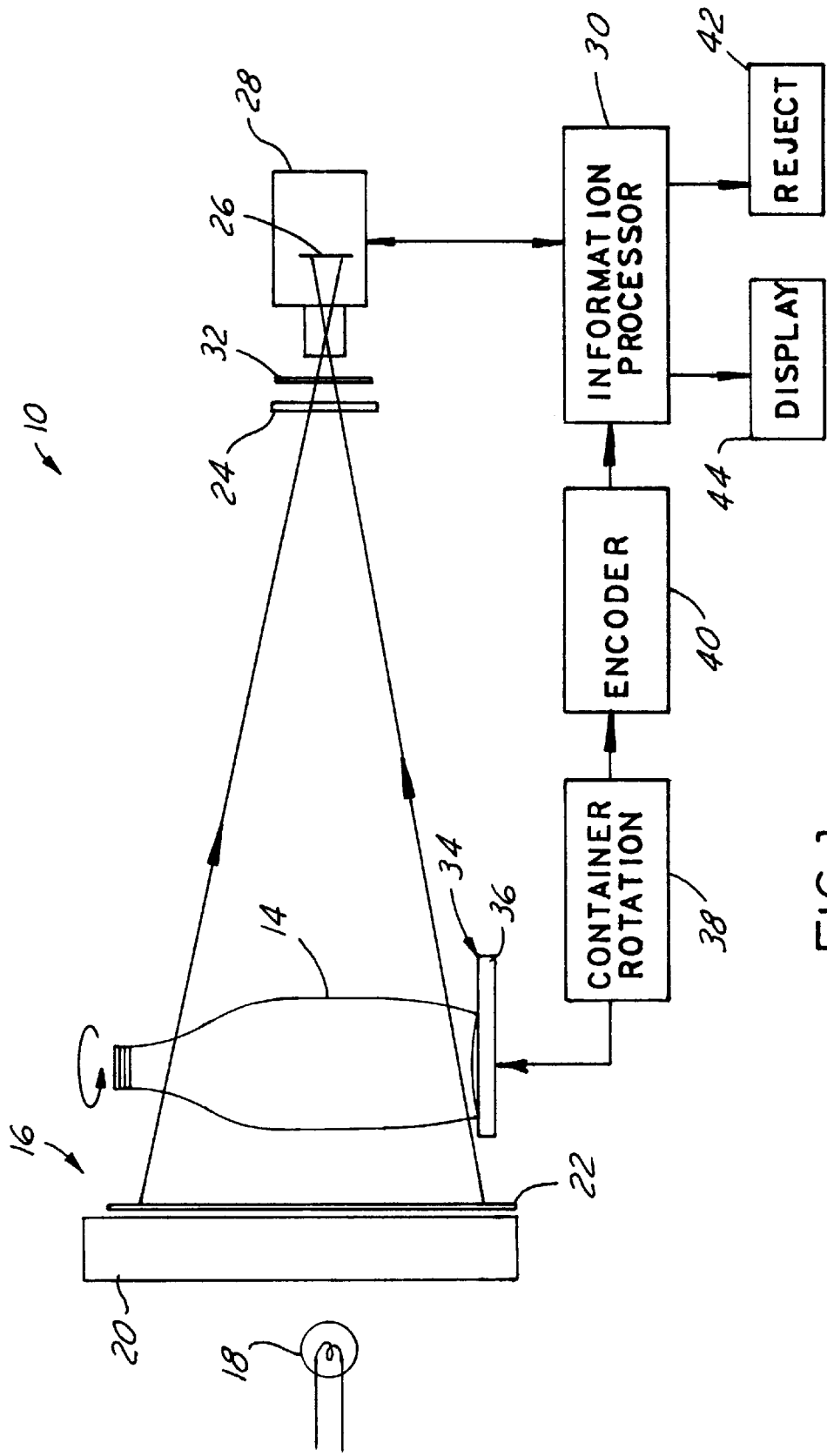
FIG. 1 is an electro-optical schematic diagram that illustrates an apparatus for detecting stress and opaque variations in the sidewalls of a container in accordance with one presently preferred embodiment of the invention.

FIG. 1 illustrates an apparatus 10 for inspecting the sidewall of a container 14 in accordance with one presently preferred embodiment of the invention. A light source 16 comprises one or more lamps 18 that cooperate with a diffuser 20 to form a broad-area diffuse light source. Light energy is directed from diffuser 20 through a first polarizer lens 22 through the sidewall of container 14, and thence through a second polarizer lens 24 onto the sensor 26 of a camera 28. Sensor 26 preferably comprises a linear array CCD sensor for providing electrical signals to an information processor 30 as a function of the one-dimensional image of container 14 focused onto array 26. A blocking filter 32 is disposed so as partially to attenuate the light energy directed onto sensor 28.

A conveyor 34, typically including a starwheel (not shown) and a slide plate 36, is so disposed and connected to a source of molded containers as to bring successive containers 14 into position at apparatus 10. Conveyor 34 may be of any suitable type, such as those shown in U.S. Pat. Nos. 4,230,219 and 4,378,493. Successive containers are held in fixed position and rotated by a device 38, such as a drive roller, about the central axis of the container. An encoder 40 is coupled to the container rotation mechanism to provide signals indicative of increments of container rotation. Such increments may comprise either fixed angular increments of rotation, or fixed time increments of rotation at a constant velocity. Information processor 30 is coupled to encoder 40 and to sensor 26 of camera 28 for scanning the sensor at increments of container rotation, and developing a two-dimensional electronic image of the container sidewall from differing angular positions with respect to the container axis. As an alternative to use of an encoder 40, information processor 30 may be controlled to scan sensor 26 at substantially equal increments of time while container 14 is rotated at substantially constant angular velocity. Sensor 26 may comprise an area array sensor, which may be scanned at increments of container rotation to develop multiple two-dimensional images of the container sidewall. Each such image would consist of light and/or dark image signals against a grey background.

In accordance with the present invention, the light energy emitted by lamp 18 through diffuser 20 comprises both visible and infrared light energy. (The visible and infrared light energies need not necessarily cover the entire wavelength ranges noted above.) Polarizers 22, 24 are at 90° orientation with respect to each other—i.e., crossed polarizers—and are constructed so as to be responsive to light energy within the visible wavelength range, while being substantially transparent to infrared light energy. Thus, incidence of light energy in the visible range onto sensor 26 is normally blocked by the crossed orientation of polarizers 22, 24. However, birefringence in the sidewall of container 14 caused by stress variations, such as stressed stones or knots, alters the angle of polarization of the light passing through the stress region, thereby producing a bright signal at sensor 26 against what would otherwise be the normally dark background of the visible light energy. In the meantime, the infrared light energy passes directly through the sidewalls of containe unless affected by opaque variations such as stress or non-stress stones. Filter 32 as responsive to light energy in the infrared range partially to attenuate such light energy, and thereby to create at sensor 26 a normally gray background, against which visible light caused by stress variations in the container sidewall appear as bright signals and infrared light blocked by opaque variations in the container sidewall appear as dark signals.

Thus, sensor 26, which is responsive to both visible and infrared energy, effectively combines the light energies from source 16 to create a normally gray background against which opaque variations appear dark and stress variations appear bright. These variations can be readily analyzed for size and type employing otherwise conventional image analysis techniques at information processor 30. See U.S. Pat. No. 4,601,395. Such information can be employed to send a reject signal 42 for removal of unsatisfactory containers from the line and/or to display image data at 44 to an operator. Exemplary techniques for scanning an area array sensor and developing two-dimensional electronic images of the container are disclosed in U.S. Pat. No. 4,958,223. The technique of the present invention thus provides improved detection of small opaque stressed stones, which will appear larger and be more easily detected because the stress pattern around the stone, as well as the stone itself, are visible to camera 28. Indeed, a stressed opaque stone will appear as a dark image of the stone surrounded by a bright image of the stressed area of the glass against a normally gray background.

Figure 3:
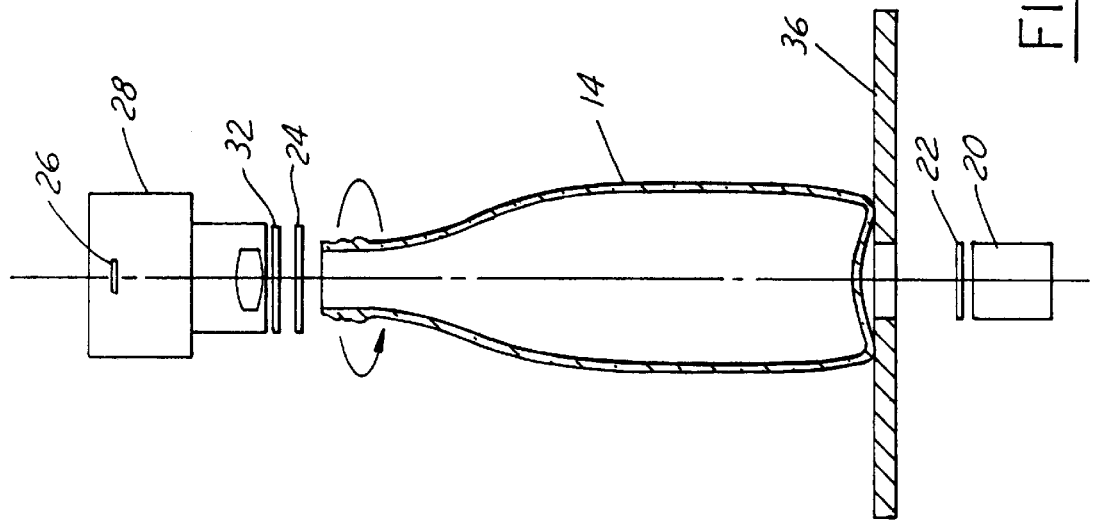
FIG. 3 is a fragmentary side view of the inspection apparatus of FIG. 2.
Figure 2:
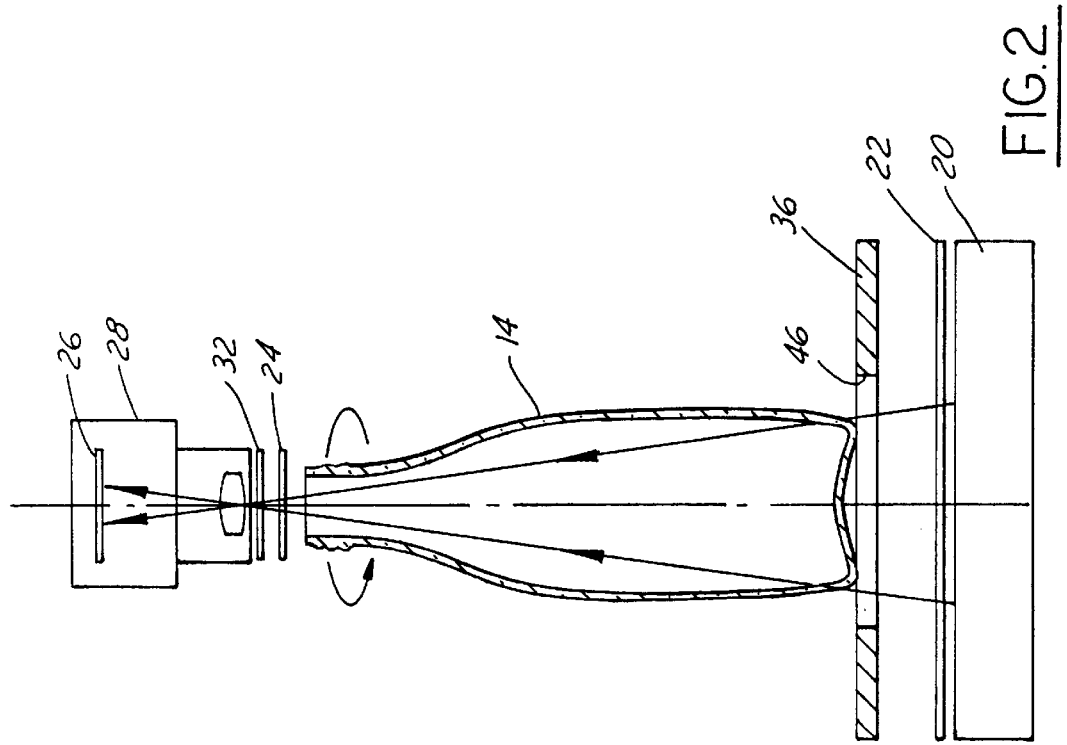
FIG. 2 is an electro-optical schematic diagram of an apparatus for detecting opaque and stress variations in the bottom of a container in accordance with another embodiment of the invention.

FIGS. 2 and 3 illustrate a second embodiment of the invention having particular utility for inspecting the bottom and heel portions of container 14. Elements that are identical or similar to those illustrated in FIG. 1 are identified by correspondingly identical reference numerals. Visible and infrared light energy is directed through a diffuser 20 and a polarizer lens 22 through an aperture 46 in slide plate 36, and then generally axially through the container bottom and heel. Camera 28, including area array sensor 26, is directed in cooperation with partial infrared filter 32 and polarizer lens 24 to receive light energy emanating from the mouth of container 14. Thus, sensor 26 cooperates with information processor 30 (FIG. 1) to develop multiple images of the container bottom, each consisting of a normally gray background against which stress variations appear as bright signals and opaque variations appear as dark signals. The light source, including diffuser 20 and polarizer lens 22, may be configured as disclosed in U.S. Pat. No. 5,466,927, assigned to the assignee hereof, whereby camera 28 may be employed at increments of container rotation to detect refractive variations in the container bottom and heel. Furthermore, although FIGS. 2 and 3 illustrate the camera receiving an image along the entire diameter of the container bottom and heel, the camera could be oriented and focused to view only a radius of the container bottom. The entire container bottom would be inspected as the bottle is rotated through one revolution.

It will also be appreciated that the techniques of the present invention for detecting opaque and stress variations may be employed in combination with other techniques for detecting refractive variations, for example, such as disclosed in above-noted U.S. Pat. No. 5,466,927 for detection of refractive characteristics in the container bottom and heel, and as disclosed in U.S. Pat. No. 4,601,395 for detection of refractive variations in the container sidewall.

There have thus been provided in accordance with the present invention a method and apparatus for inspecting glass articles such as containers for commercial variations that affect the optical characteristics of the containers, particularly stress variations and opaque variations in the containers. The method and apparatus of the invention may be implemented employing relatively inexpensive polarizer material responsive to light energy in the visible range, as distinguished from more expensive polarizer material responsive to light energy in the infrared range. The techniques of the invention may be readily employed in connection with both clear (flint) and colored (e.g., amber) glass. The method and system of the invention may be implemented at a single container inspection station, and employing a single light source and a single light sensor as described.

I claim:

1. A method of inspecting containers for commercial variations that affect optical characteristics of the containers, which comprises the steps of:
   (a) directing light energy onto a container in such a way that a first wavelength of the light energy is responsive to a first type of commercial variation in the container and a second wavelength of the light energy different from said first wavelength is responsive to a second type of commercial variation different from said first type,
   (b) detecting light energy from the container onto light sensing means, and
   (c) detecting commercial variations of said first and second types at the container as a function of a comparison between light energies at said first and second wavelengths incident on said light sensing means by forming an image at said light sensing means of light energy at said first wavelength against a background of energy at said second wavelength.

2. The method set forth in claim 1 comprising the additional step of: (d) providing said light sensing means in the form of a single sensor responsive to light energy at both of said first and second wavelengths.

3. The method set forth in claim 2 wherein said light energies at said first and second wavelengths are incident simultaneously on said single sensor.

4. The method set forth in claim 1 wherein said sensing means comprises an area array sensor for providing a two-dimensional image that consists of light energy received at said first wavelength against a background of light energy received at said second wavelength.

5. The method set forth in claim 4 wherein said light energy at said first wavelength comprises visible light energy, and said light energy at said second wavelength comprises infrared light energy.

6. The method set forth in claim 5 wherein said visible light energy comprises polarized light energy.

7. The method set forth in claim 5 wherein said visible light energy is within the wavelength range of about 0.4 to 0.7 micrometers, and said infrared light energy is within the wavelength range of about 0.7 to 300 micrometers.

8. The method set forth in claim 7 wherein said containers are glass containers, and wherein said infrared energy is in the range of about 0.7 to 5 micrometers.

9. The method set forth in claim 8 wherein said infrared energy is in the range of about 0.7 to 1.1 micrometers.

10. The method set forth in claim 1 comprising the additional steps of:
   (d) polarizing said energy at one of said first and second wavelengths in such a way that only light energy at said one wavelength that passes through a stress variation at the containers is incident on said sensing means, and
   (e) partially attenuating light energy at the other of said first and second wavelengths.

11. The method set forth in claim 1 comprising the additional steps of:
   (d) rotating the container about its central axis, and
   (e) performing said step (c) at increments of container rotation.

12. The method set forth in claim 1 for inspecting a container sidewall wherein said steps (a) and (b) comprise the step of directing said light energies simultaneously onto the container sidewall.

13. The method set forth in claim 1 for inspecting a container bottom wherein said steps (a) and (b) comprise the step of directing said light energies simultaneously into the container bottom.

14. The method set forth in claim 1 comprising the additional step of: (d) detecting commercial variations of a third type different from said first and second types as a function of at least one of said light energies at said sensing means.

15. Apparatus for detection of stress variations and opaque variations in containers, which comprises:
   light sensing means for producing electrical signals responsive to light energy incident thereon in visible and infrared ranges,
   first means for directing infrared light energy through a container onto said light sensing means in such a way as to create at said light sensing means a normally gray background, and such that opaque variations in the container appear as dark signals against said gray background, second means, including crossed polarizers disposed on opposite sides of the container, for directing visible light energy through the container and onto said light sensing means in such a way that stress variations in the container appear as bright signals against the gray background at said light sensing means, and means coupled to said light sensing means for detecting such stress and opaque variations as a function of said bright and dark signals against said gray background.

16. The apparatus set forth in claim 15 wherein said first and second means comprise a single light source for directing said visible and infrared light energies through the container and onto said light sensing means simultaneously.

17. The apparatus set forth in claim 16 wherein said light sensing means comprises a single light sensor.

18. The apparatus set forth in claim 17 wherein said single light sensor comprises an array sensor for receiving an image of the container that includes said light and dark signals against said gray background.

19. The apparatus set forth in claim 18 further comprising means for rotating the container about its axis, and means for scanning said light sensor at increments of container rotation.

20. A method of inspecting transparent glass articles for stress variations and opaque variations that comprises the steps of:

(a) directing light energies at first and second wavelength ranges through an article simultaneously onto a single light sensor, (b) partially attenuating one of said light energy wavelength ranges so as to create a gray background at said sensor against which an opaque variation at the article appears as a dark image against said gray background, (c) polarizing the other of said wavelength ranges such that a stress variation at the article appears as a light image against said gray background, and (d) detecting stress and opaque variations in the article as a function of said light and dark images.

21. The method set forth in claim 18 wherein said sensor comprises a CCD sensor that receives an image consisting of said light and dark images against said gray background.

22. The method set forth in claim 21 wherein said step (a) comprises the step of generating light energy at both of said wavelength ranges from a single light source.

23. The method set forth in claim 22 wherein said single light source comprises a broad area diffuse light source.

* * * * *

UNITED STATES PATENT AND TRADEMARK OFFICE
CERTIFICATE OF CORRECTION

PATENT NO. : 6,067,155
DATED : May 23, 2000
INVENTOR(S) : James A. Ringlien

It is certified that error appears in the above-identified patent and that said Letters Patent is hereby corrected as shown below:

Claim 1, column 5,
Subparagraph (b), line 64, the word "detecting" should read -- directing --.

Signed and Sealed this

Second Day of October, 2001

Attest:

*Nicholas P. Godici*

NICHOLAS P. GODICI
*Attesting Officer*     *Acting Director of the United States Patent and Trademark Office*